(12) United States Patent
Han

(10) Patent No.: US 10,448,928 B2
(45) Date of Patent: Oct. 22, 2019

(54) METHOD AND DEVICE FOR DETECTING PHYSIOLOGICAL INDEX

(71) Applicant: BOE TECHNOLOGY GROUP CO., LTD., Beijing (CN)

(72) Inventor: Yanling Han, Beijing (CN)

(73) Assignee: BOE Technology Group Co., Ltd., Beijing (CN)

(*) Notice: Subject to any disclaimer, the term of this patent is extended or adjusted under 35 U.S.C. 154(b) by 444 days.

(21) Appl. No.: 15/100,761

(22) PCT Filed: Oct. 29, 2015

(86) PCT No.: PCT/CN2015/093229
§ 371 (c)(1),
(2) Date: Jun. 1, 2016

(87) PCT Pub. No.: WO2016/206267
PCT Pub. Date: Dec. 29, 2016

(65) Prior Publication Data
US 2017/0128052 A1    May 11, 2017

(30) Foreign Application Priority Data
Jun. 25, 2015 (CN) .......................... 2015 1 0359441

(51) Int. Cl.
*A61B 10/00* (2006.01)
*A61B 5/00* (2006.01)
(Continued)

(52) U.S. Cl.
CPC ........ *A61B 10/0012* (2013.01); *A61B 5/0008* (2013.01); *A61B 5/01* (2013.01);
(Continued)

(58) Field of Classification Search
CPC .......... A61B 2010/0019; A61B 5/0008; A61B 2562/0271; A61B 5/01
See application file for complete search history.

(56) References Cited

U.S. PATENT DOCUMENTS 4,151,831 A * 5/1979 Lester ...................... A61B 5/01
368/10
6,530,945 B1    3/2003 Noda et al.
(Continued)

FOREIGN PATENT DOCUMENTS

CN    103479337 A *  1/2014
CN    103876783 A    6/2014
(Continued)

OTHER PUBLICATIONS

International Search Report of PCT/CN2015/093229 in Chinese, dated Mar. 18, 2016 with English translation.
(Continued)

*Primary Examiner* — Sean P Dougherty
*Assistant Examiner* — Nicholas E Kolderman
(74) *Attorney, Agent, or Firm* — Collard & Roe, P.C.

(57) ABSTRACT

A method and a device for detecting physiological indexes. The method includes: obtaining a body temperature fluctuation value associated with a user, where the body temperature fluctuation value is at least obtained by a first difference value between a current shell temperature associated with the user and a basal temperature associated with the user (101); and determining a current physiological index associated with the user based on the body temperature fluctuation value associated with the user (102). The method can be applicable in a detection process for physiological indexes and can perform health-related operations based on the detected physiological indexes including a body temperature measuring result.

16 Claims, 5 Drawing Sheets

(51) Int. Cl.
*A61B 5/01* (2006.01)
*G16H 50/30* (2018.01)
*G16H 40/63* (2018.01)
*G16H 50/70* (2018.01)
*G16H 50/20* (2018.01)

(52) U.S. Cl.
CPC ............ *A61B 5/681* (2013.01); *A61B 5/7275* (2013.01); *A61B 5/742* (2013.01); *A61B 5/7415* (2013.01); *A61B 5/7475* (2013.01); *G16H 40/63* (2018.01); *G16H 50/30* (2018.01); *G16H 50/70* (2018.01); *A61B 2010/0019* (2013.01); *A61B 2560/0252* (2013.01); *A61B 2562/0271* (2013.01); *G16H 50/20* (2018.01)

(56) References Cited

U.S. PATENT DOCUMENTS

| | | | | |
|---|---|---|---|---|
| 2005/0245839 | A1* | 11/2005 | Stivoric | A61B 5/0008 600/549 |
| 2011/0243183 | A1 | 10/2011 | Goto | |
| 2012/0238900 | A1* | 9/2012 | Rechberg | A61B 5/01 600/549 |
| 2012/0265032 | A1* | 10/2012 | Ben-David | A61B 5/01 600/301 |
| 2015/0133744 | A1* | 5/2015 | Kobayashi | A61B 10/0012 600/301 |

FOREIGN PATENT DOCUMENTS

| | | |
|---|---|---|
| CN | 103932683 A | 7/2014 |
| CN | 104224121 A | 12/2014 |
| CN | 104271048 A | 1/2015 |
| CN | 104305967 A | 1/2015 |
| CN | 204072159 U | 1/2015 |
| CN | 104352253 A | 2/2015 |
| CN | 104523244 A | 4/2015 |
| CN | 104887194 A | 9/2015 |
| JP | 2001-004453 A | 1/2001 |
| WO | 02/43577 A2 | 6/2002 |

OTHER PUBLICATIONS

Notice of Transmittal of the International Search Report of PCT/CN2015/093229 in Chinese, dated Mar. 18, 2016.
Written Opinion of the International Searching Authority of PCT/CN2015/093229 in Chinese, dated Mar. 18, 2016 with English translation.
Chinese Office Action in Chinese Application No. 201510359441.5, dated Feb. 4, 2017 with English translation.
Second Chinese Office Action in Chinese Application No. 201510359441.5, dated Sep. 14, 2017 with English translation.

* cited by examiner

METHOD AND DEVICE FOR DETECTING PHYSIOLOGICAL INDEX

CROSS REFERENCE TO RELATED APPLICATIONS

This application is the National Stage of PCT/CN2015/093229 filed on Oct. 29, 2015, which claims priority under 35 U.S.C. § 119 of Chinese Application No. 201510359441.5 filed on Jun. 25, 2015, the disclosure of which is incorporated by reference.

TECHNICAL FIELD

Embodiments of the present disclosure relate to a method and device for detecting physiological indexes.

BACKGROUND

Body temperature is one of the important vital signs of human body and can effectively reflect physical health condition. Thus, temperature monitoring is widely applied in clinical medicine. Temperature monitoring, also known as temperature measurement, refers to testing and measuring the body temperature so as to provide basis for disease diagnosis and treatment.

At present, a widely used temperature monitoring manner generally includes measuring a shell temperature of a user through a thermometer. However, as most users do not have professional medical knowledge, especially for special groups with large or relatively frequent body temperature fluctuation such as children, the elderly and women in menstruation, health-related suggestions cannot be scientifically and conveniently provided according to the measurement results of the body temperature.

SUMMARY

Embodiments of the present disclosure provide a method and device for detecting physiological indexes. Health-related suggestions can be scientifically and conveniently provided according to the measurement results of the body temperature.

At least one embodiment of the present disclosure provides a method for detecting physiological indexes, including:

obtaining a body temperature fluctuation value associated with a user, where the body temperature fluctuation value is at least obtained by a first difference value between a current shell temperature associated with the user and a basal temperature associated with the user; and determining a current physiological index associated with the user based on the body temperature fluctuation value associated with the user.

For example, the physiological index includes physiological cycle data. Prior to determining the current physiological index associated with the user based on the body temperature fluctuation value associated with the user, the method further includes obtaining basic physiological cycle data associated with the user, where the basic physiological cycle data includes a quantity of days of one menstrual cycle, a starting date of menstruation and an end date of menstruation. Determining the current physiological index associated with the user based on the body temperature fluctuation value associated with the user includes: predicting a current physiological cycle associated with the user based on the basic physiological cycle data associated with the user to obtain predicted physiological cycle data; and correcting the predicted physiological cycle data based on the body temperature fluctuation value associated with the user to determine actual physiological cycle data associated with the user.

For example, obtaining the basic physiological cycle data associated with the user includes: receiving the basic physiological cycle data inputted by the user.

For example, the physiological index includes body temperature fluctuation data. Determining the current physiological index associated with the user based on the body temperature fluctuation value associated with the user includes: determining that the body temperature fluctuation data associated with the user is normal if the body temperature fluctuation value is within a pre-configured normal temperature range; determining that the body temperature fluctuation data associated with the user is comparatively high if the body temperature fluctuation value is within a pre-configured positive temperature range; and determining that the body temperature fluctuation data associated with the user is comparatively low if the body temperature fluctuation value is within a pre-configured negative temperature range.

For example, after determining the current physiological index associated with the user based on the body temperature fluctuation value associated with the user, the method further includes: sending back the body temperature fluctuation data to the user through at least one of a display, an indicator light and specified music; or sending the body temperature fluctuation data to client devices of other users via wireless or wired connection.

For example, obtaining the first difference value includes: detecting the shell temperature associated with the user within a first predetermined time window before this physiological index detection and the current shell temperature associated with the user; calculating an average value of the shell temperature associated with the user within the first predetermined time window, and determining the average value of the shell temperature associated with the user to be the basal body temperature associated with the user; and determining a difference value between the current shell temperature associated with the user and the basal body temperature associated with the user to be the first difference value.

For example, the body temperature fluctuation value is obtained by the first difference value between the current shell temperature associated with the user and the basal body temperature associated with the user and a second difference value between a current ambient temperature and an ambient reference temperature. Determining the current physiological index associated with the user based on the body temperature fluctuation value associated with the user includes: determining the current physiological index associated with the user based on a difference value between the first difference value and the second difference value.

For example, obtaining the second difference value includes: detecting the ambient temperature within a second predetermined time window before this physiological index detection and the current ambient temperature; calculating an average value of the ambient temperature within the second predetermined time window, and determining the average value of the ambient temperature within the second predetermined time window to be the ambient reference temperature; and determining a difference value between the current ambient temperature and the ambient reference temperature to be the second difference value.

Another embodiment of the present disclosure provides a device for detecting physiological indexes, including: an acquisition unit configured to obtain a body temperature fluctuation value associated with a user, where the body temperature fluctuation value is at least obtained by a first difference value between a current shell temperature associated with the user and a basal body temperature associated with the user; and a determination unit configured to determine a current physiological index based on the body temperature fluctuation value associated with the user.

For example, the physiological index includes physiological cycle data. The acquisition unit is configured to obtain basic physiological cycle data associated with the user, where the basic physiological cycle data includes a quantity of days of one menstrual cycle, a starting date of menstruation and an end date of menstruation. The determination unit is configured to: predict a current physiological cycle associated with the user based on the basic physiological cycle data associated with the user to obtain predicted physiological cycle data; and correct the predicted physiological cycle data based on the body temperature fluctuation value associated with the user to determine actual physiological cycle data associated with the user.

For example, the acquisition unit is configured to receive the basic physiological cycle data inputted by the user.

For example, the physiological index includes body temperature fluctuation data. The determination unit determines that the body temperature fluctuation data associated with the user is normal if the body temperature fluctuation value is within a pre-configured normal temperature range; the determination unit determines that the body temperature fluctuation data associated with the user is comparatively high if the body temperature fluctuation value is within a pre-configured positive temperature range; and the determination unit determines that the body temperature fluctuation data associated with the user is comparatively low if the body temperature fluctuation value is within a pre-configured negative temperature range.

For example, the device further includes a transmission unit. The transmission unit is configured to send back the body temperature fluctuation data to the user through at least one of a display, an indicator light and specified music; or the transmission unit is configured to send the body temperature fluctuation data to client devices of other users via wireless or wired connection.

For example, the body temperature fluctuation value is obtained by the first difference value between the current shell temperature associated with the user and the basal body temperature associated with the user and a second difference value between a current ambient temperature and an ambient reference temperature. The determination unit is configured to determine the current physiological index associated with the user based on a difference value between the first difference value and the second difference value.

For example, the acquisition unit of the device includes a temperature detection unit, a storage unit and a calculating unit. The temperature detection unit is configured to detect the shell temperature associated with the user within a first predetermined time window before this physiological index detection and the current shell temperature associated with the user, and send the detected data to the storage unit. The calculating unit is configured to: calculate an average value of the shell temperature associated with the user within the first predetermined time window based on the detected shell temperature associated with the user within the first predetermined time window stored in the storage unit; determine the average value of the shell temperature associated with the user to be the basal body temperature associated with the user; and determine a difference value between the current shell temperature associated with the user stored in the storage unit and the basal body temperature associated with the user to be the first difference value.

For example, the temperature detection unit is also configured to detect the ambient temperature within a second predetermined time window before this physiological index detection and the current ambient temperature, and send the detected data to the storage unit. The calculating unit is configured to: calculate an average value of the ambient temperature within the second predetermined time window based on the detected ambient temperature within the second predetermined time window stored in the storage unit; determine the average value of the ambient temperature within the second predetermined time window to be the ambient reference temperature; determine a difference value between the current ambient temperature stored in the storage unit and the ambient reference temperature to be the second difference value; and use a difference value between the first difference value and the second difference value to be the body temperature fluctuation value.

For example, the device for detecting the physiological indexes is a wearable bracelet.

Embodiments of the present disclosure provide a method and device for detecting physiological indexes. In the method and the device, a body temperature fluctuation value of a user is acquired. The body temperature fluctuation value includes a first difference value between a current shell temperature of the user and a basal body temperature of the user. Or, the body temperature fluctuation value includes a difference value of the first difference value between the current shell temperature of the user and the basal body temperature of the user and a second difference value between a current ambient temperature and an ambient reference temperature. Subsequently, current physiological indexes of the user are determined according to the body temperature fluctuation value of the user. The physiological indexes may include body temperature fluctuation data and/or physiological cycle data. Because the device for detecting the physiological indexes can determine the physiological indexes of the user based on the body temperature fluctuation value of the user, health-related suggestions can be scientifically provided according to the body temperature fluctuation value of the user, so that the user can obtain the physiological indexes quickly and accurately.

BRIEF DESCRIPTION OF THE DRAWINGS

In order to illustrate the technical solutions in the embodiments of the present disclosure or the existing arts more clearly, the drawings need to be used in the description of the embodiments or the existing arts will be briefly described in the following; it is obvious that the drawings described below are only related to some embodiments of the present disclosure, for one ordinary skilled person in the art, other drawings can be obtained according to these drawings.

DETAILED DESCRIPTION

Hereafter, the technical solutions of the embodiments of the present disclosure will be described in a clearly and fully understandable way in connection with the drawings related to the embodiments of the disclosure. It is obvious that the described embodiments are just a part but not all of the embodiments of the present disclosure. The drawings mentioned in the embodiments of the present disclosure are only to exemplarily illustrate the technical solutions of the present disclosure. The other drawings obtained from the drawings of the embodiments of the present disclosure through simple transformations should be within the scope of the present disclosure.

First Embodiment

Figure 1:
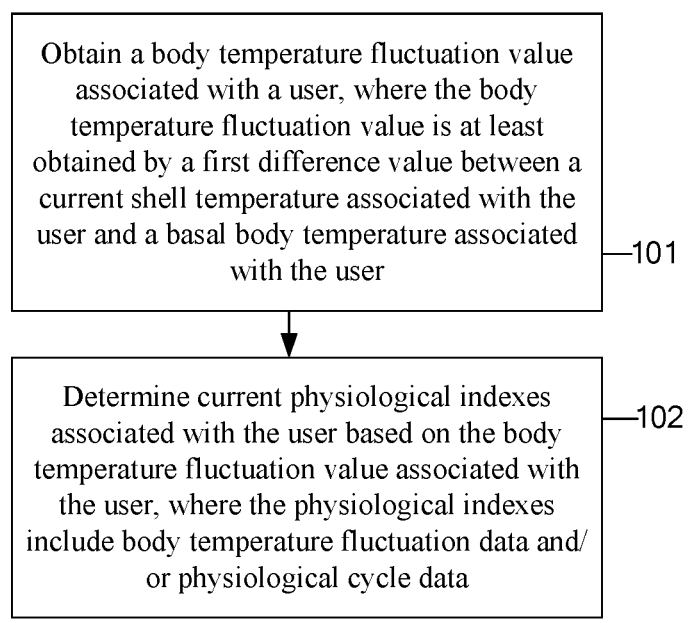
FIG. 1 is a first flowchart of a method for predicting physiological cycles provided by a first embodiment of the present disclosure.

The first embodiment of the present disclosure provides a method for detecting physiological indexes. As illustrated in FIG. 1, the method includes:

Step 101: obtaining a body temperature fluctuation value associated with a user, where the body temperature fluctuation value is at least obtained by a first difference value between a current shell temperature associated with the user and a basal body temperature associated with the user; and Step 102: determining current physiological indexes associated with the user based on the body temperature fluctuation value associated with the user, where the physiological indexes include body temperature fluctuation data and/or physiological cycle data.

The method for detecting the physiological indexes, provided by the first embodiment of the present disclosure, may be applied in a device for detecting the physiological indexes. The device for detecting the physiological indexes may be any wearable device, e.g., a wearable wrist watch, a wearable headset or a wearable bracelet. Because the wearable device can be conveniently carried by the user, detection of the physiological indexes via the wearable device can simplify the process of detecting the physiological indexes. For instance, detailed description will be given in the subsequent embodiments by taking a wearable bracelet as an example device for detecting the physiological indexes.

For instance, in the step 101, the wearable bracelet may determine a body temperature fluctuation state of the user by obtaining the body temperature fluctuation value of the user, and subsequently analyze the current physiological indexes of the user according to the body temperature fluctuation state of the user, e.g., whether the body temperature is too high, whether more clothes are needed to be put on, or whether the user has entered an ovulation period, etc.

In order to acquire the body temperature fluctuation value of the user, the wearable bracelet may acquire the basal body temperature T0 (T0>0) of the user at first, subsequently detect the current shell temperature of the user (namely a current body temperature T1 (T1>0)) through a first temperature sensor in the wearable bracelet, and then obtain a first difference value between the current shell temperature T1 of the user and the basal body temperature T0 of the user (e.g., the first difference value being a body temperature fluctuation value of the user). The first temperature sensor in the wearable bracelet may be disposed at a position that contacts with the skin of the user. For instance, the first temperature sensor may be disposed in an inner side of the wearable bracelet and make contact with the wrist of the user or the axilla of the user, and hence detect the shell temperature of the user.

For instance, as the body temperature of a normal person is usually maintained at 37 degrees or so, a basal body temperature T0 of any user may be stored as 37 degrees in the wearable bracelet. Of course, a basal body temperature T0 of a user may also be set in the wearable bracelet by the user.

In addition, a first temperature sensor in the wearable bracelet may periodically measure the body temperature of the user. Thus, the basal body temperature T0 of the user may be an average value of the body temperature of the user detected by the first temperature sensor within a first predetermined time window before this physiological index detection, or the basal body temperature T0 of the user may be an average value of the body temperature of the user detected by the first temperature sensor in previous detection periods. No limitation will be placed here in embodiments of the present disclosure.

Moreover, the environment surrounding the user may be varied in real time and the body temperature of the user may also be affected by the ambient temperature. Thus, in order to more accurately detect the current physiological indexes of the user, a variation factor such as the ambient temperature may be considered in the process of calculating the body temperature fluctuation value of the user.

In this case, the body temperature fluctuation value of the user may be a difference value between the first difference value and the second difference value. The second difference value is a difference value between a current ambient temperature H1 and an ambient reference temperature H0.

For instance, the wearable bracelet may detect the ambient temperature within a second predetermined time window before this physiological index detection through a second temperature sensor configured in the wearable bracelet, and calculate an average value of the ambient temperature within the second predetermined time window to obtain the ambient reference temperature H0. Subsequently, the wearable bracelet detects the current ambient temperature H1 through the second temperature sensor and obtains a difference value (namely a second difference value) between the current ambient temperature H1 and the ambient reference temperature H0.

That is, the body temperature fluctuation value=the first difference value−the second difference value=T1−T0−(H1−H0).

Thus, the wearable bracelet may acquire the body temperature fluctuation value of the user through the first temperature sensor and the second temperature sensor, so as to determine the body temperature fluctuation state of the user.

In the step 102, the wearable bracelet may determine current physiological indexes of the user based on the body temperature fluctuation value of the user acquired in the step 101. The physiological indexes may include at least one of body temperature fluctuation data and actual physiological cycle data.

For instance, when the physiological indexes include the body temperature fluctuation data of the user and −0.5° C.<the body temperature fluctuation value<0.5° C., it indicates that the body temperature fluctuation data of the user is normal, so that the wearable bracelet can indicate a normal body temperature for the user; when −1° C.<the body temperature fluctuation value<−0.5° C., it indicates that the body temperature fluctuation data of the user is comparatively low, so that the wearable bracelet can suggest wearing more clothes for the user; when 0.5° C.<the body temperature fluctuation value<1° C., it indicates that the body temperature fluctuation data of the user is comparatively high, so that the wearable bracelet can suggest wearing less clothes for the user; when the body temperature fluctuation value<−1° C., it indicates that the body temperature fluctuation data of the user is too low, so that the wearable bracelet can indicate a risk of catching a cold for the user; and when the body temperature fluctuation value>1° C., it indicates that the body temperature fluctuation data of the user is too high, so that the wearable bracelet can indicate a risk of having a fever for the user.

For instance, the wearable bracelet may feed back the body temperature fluctuation data to the user via one or more ways including displaying with an indicator, displaying text or a pattern on a display, playing specified music or the like, so as to provide corresponding health suggestions to the user.

The wearable bracelet may also send the determined body temperature fluctuation data to client devices of other users via wireless connection (e.g., WiFi function, bluetooth function and infrared function) or wired connection (e.g., data line connection). For instance, an indication of too high body temperature fluctuation data of a child is sent to client devices of the child's parents, so that the parents can acquire the body temperature fluctuation of the child in time and hence can let the child wear fewer clothes or take measures to reduce the temperature of the child, etc.

Figure 2:
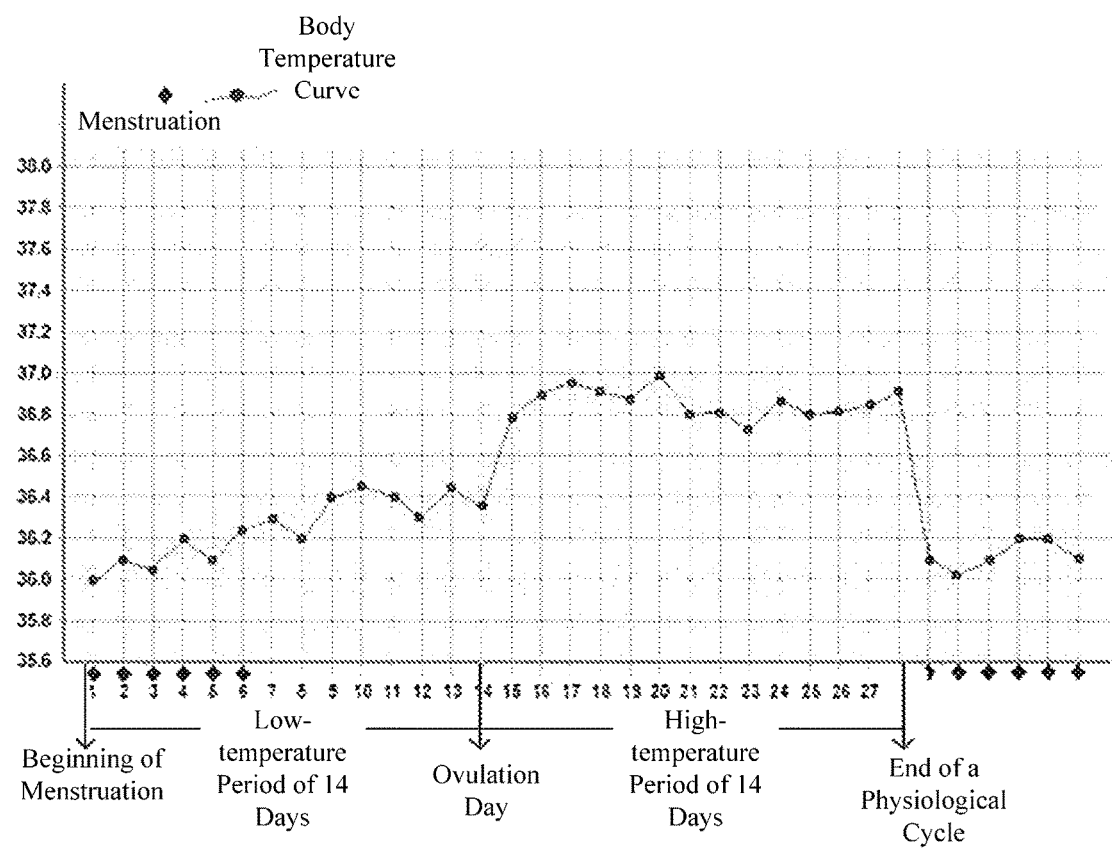
FIG. 2 is a schematic diagram of a temperature fluctuation curve of a female in one physiological cycle.

In addition, the body temperature level of an adult female fluctuates in different phases of the physiological cycle. As illustrated in FIG. 2, the body temperature is higher before menstruation; the body temperature is reduced by 0.2-0.3° C. or so at the beginning of menstruation; and the body temperature is reduced by 0.2° C. or so at first and then suddenly increased by 0.4° C. or so in the ovulatory period. That is, in one month there is a bidirectional curve in which the body temperature is low in a first period and high in a later period.

Therefore, the wearable bracelet may also analyze and detect the current physiological cycle data of the user based on the body temperature fluctuation value of the user.

For instance, when the wearable bracelet detects that the body temperature fluctuation value of the user is −0.2° C. (that is, the body temperature of the user is suddenly reduced), the wearable bracelet can determine that the user is about to enter the ovulatory period or to start menstruation. At this point, the wearable bracelet can send the determined actual physiological cycle data to the display device of the wearable bracelet to remind the user of the current physiological cycle period. For instance, the wearable bracelet is provided with light bars with different colors to correspond to different phases in a physiological cycle, and hence reminds the user of reasonable arrangements for travel or the like according to the different phases in a physiological cycle.

Detailed description will be given in the subsequent embodiments for methods of detecting the current physiological cycle data of the user according to the body temperature fluctuation value of the user via the wearable bracelet. Repeated description will not be given here.

Thus, the method for detecting the physiological indexes, provided by the first embodiment of the present disclosure, includes: obtaining the body temperature fluctuation value of the user, where the body temperature fluctuation value includes the first difference value between the current shell temperature of the user and the basal body temperature of the user; and subsequently, determining the current physiological indexes of the user based on the body temperature fluctuation value of the user, where the physiological indexes may include the body temperature fluctuation data and/or the physiological cycle data. Because the device for detecting the physiological indexes, which employs the method for detecting the physiological indexes provided by the first embodiment of the present disclosure, can determine the physiological indexes of the user according to the body temperature fluctuation value of the user, health-related data processing can be performed more scientifically according to the body temperature fluctuation value of the user, so that the user can obtain the physiological indexes quickly and accurately.

Second Embodiment

Figure 3:
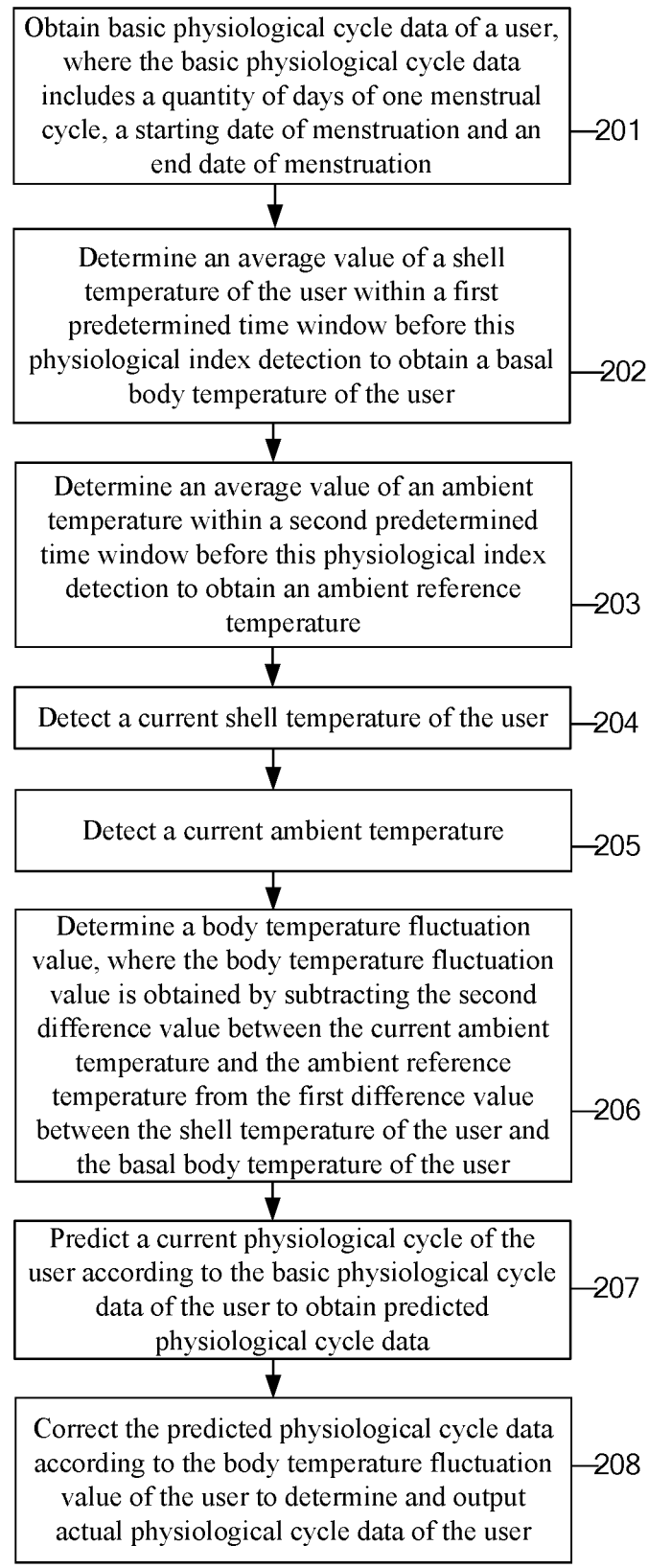
FIG. 3 is another flowchart of a method for predicting physiological cycles provided by a second embodiment of the present disclosure.

The second embodiment of the present disclosure provides a method for detecting physiological indexes. As illustrated in FIG. 3, the method includes:

Step 201: obtaining basic physiological cycle data of a user, where the basic physiological cycle data includes a quantity of days of one menstrual cycle, a starting date of menstruation and an end date of menstruation;

Step 202: determining an average value of a shell temperature of the user within a first predetermined time window before this physiological index detection to obtain a basal body temperature of the user;

Step 203: determining an average value of an ambient temperature within a second predetermined time window before this physiological index detection to obtain an ambient reference temperature;

Step 204: detecting a current shell temperature of the user;

Step 205: detecting a current ambient temperature;

Step 206: determining a body temperature fluctuation value, where the body temperature fluctuation value is obtained by subtracting the second difference value between the current ambient temperature and the ambient reference temperature from the first difference value between the shell temperature of the user and the basal body temperature of the user;

Step 207: predicting a current physiological cycle of the user according to the basic physiological cycle data of the user to obtain predicted physiological cycle data; and Step 208: correcting the predicted physiological cycle data according to the body temperature fluctuation value of the user to determine and output actual physiological cycle data of the user.

In the step 201, a wearable bracelet may receive the basic physiological cycle data inputted by the user. The basic physiological cycle data includes the number of days of one menstrual cycle, the starting date of menstruation and the end date of menstruation.

For instance, the number of days of one menstrual cycle inputted by the user is 28; the starting date of menstruation is May 1; and the end date of menstruation is May 7. Since a normal female of child-bearing age undergoes one menstruation each month, a period from the beginning of this menstruation to a first day of the beginning of a next menstruation may be referred to as one physiological cycle, and each physiological cycle may be divided into a post-menstruation period, an ovulatory period, a pre-menstrual period and a menstrual period. Therefore, the wearable bracelet can simply predict the physiological cycle of the user according to the basic physiological cycle data, for example, predicting the starting date of the next menstruation to be May 29.

Of course, the basic physiological cycle data may further include other data, e.g., a dysmenorrhea scale and a menstrual blood volume (MBV). Correspondingly, a data model based on each of the basic physiological cycle data may be established in the wearable bracelet, so that the wearable bracelet can predict the physiological cycle of the user more accurately based on the basic physiological cycle data.

In addition, as the wearable bracelet may periodically detect the physiological cycle of the user, the basic physiological cycle data may also include a detection result of the physiological cycle data of the user obtained by the wearable bracelet at the time when a previous detection cycle ends. In this case, the basic physiological cycle data is not needed to be manually inputted by the user each time.

In the step 202, the wearable bracelet may detect the shell temperature of the user within the first predetermined time window before this physiological index detection through a first temperature sensor disposed in the wearable bracelet, and calculate an average value of the shell temperature of the user within the first predetermined time window to obtain the basal body temperature T0 of the user. That is, the average temperature value of the user within the first predetermined time window before this physiological index detection is T0.

For instance, as the body temperature is relatively stable at about 8:00 AM, about 3:00 PM and about 8:00 PM, an average value of the body temperature detected at about 8:00 AM, about 3:00 PM and about 8:00 PM in one day before this physiological index detection may be calculated, and the average value of the body temperature is taken as the basal body temperature T0 of this physiological index detection.

In the step 203, as the environment surrounding the user may be varied in real time, the body temperature of the user may also be affected by the ambient temperature. Thus, in order to detect the current physiological cycle data of the user more accurately, the variation factor of the ambient temperature may be considered in the process of calculating the body temperature fluctuation value of the user.

For instance, the wearable bracelet may detect the ambient temperature of the environment within a second predetermined time window before this physiological index detection through a second temperature sensor disposed in the wearable bracelet, and calculate an average value of the ambient temperature within the second predetermined time window to obtain the ambient reference temperature H0. That is, the average value of the ambient temperature within the second predetermined time window before this physiological index detection is H0.

For instance, the second temperature sensor may be disposed at a position on an outer side of the wearable bracelet to have contact with the external environment, so that the second temperature sensor can accurately detect the ambient temperature.

In addition, the second predetermined time window may be the same as the first predetermined time window in the step 202.

In the steps 204 and 205, in order to accurately calculate the current body temperature fluctuation state of the user, the first temperature sensor may be continuously used to detect the current shell temperature T1 of the user and the second temperature sensor may be used to detect the current ambient temperature H1.

It should be noted that no limitation is given to the execution sequence of the steps 202 and 203; the step 202 may be executed before and after the step 203; and the step 202 may also be executed at the same time with the step 203. Similarly, no limitation is given to the execution sequence of the steps 204 and 205; the step 204 may be executed before or after the step 205; and the step 204 may also be executed at the same time with the step 205.

Moreover, in the step 206, the wearable bracelet may calculate the body temperature fluctuation value of the user based on the first difference value between the shell temperature T1 of the user and the basal body temperature T0 of the user and the second difference value between the current ambient temperature H1 and the ambient reference temperature H0.

That is, the body temperature fluctuation value=the first difference value−the second difference value=T1−T0−(H1−H0).

Thus, the body temperature fluctuation value of the user is calculated through the above formula. As the influence of the variation of the ambient temperature on the body temperature of the user is taken into full consideration, the calculated body temperature fluctuation value is more accurate, so that the wearable bracelet can conveniently determine the physiological cycle data of the user according to the body temperature fluctuation value.

In the step 207, the wearable bracelet predicts the current physiological cycle of the user based on the basic physiological cycle data in the step 201, and obtains the predicted physiological cycle data.

With reference to relevant description in the step 201, a data model based on each of the basic physiological cycle data may be established in the wearable bracelet. The wearable bracelet can predict the physiological cycle of the user according to the basic physiological cycle data obtained in the step 201, and obtain the predicated physiological cycle data.

It should be noted that the step 207 may be executed at any moment after the step 201 and before the step 208. No limitation will be given here in the present disclosure.

In the step 208, as the body temperature level of an adult female fluctuates in different phases of the physiological cycle (as illustrated in FIG. 2, the body temperature is comparatively high before menstruation; the body temperature is reduced by about 0.2-0.3° C. at the beginning of menstruation; and the body temperature is reduced by about 0.2° C. at first and then suddenly increased by about 0.4° C. in the ovulation period; that is, in one month there is a bidirectional curve in which the body temperature is low in the first period and high in the later period), the wearable bracelet corrects the predicted physiological cycle data obtained in the step 207 based on the body temperature fluctuation value of the user acquired in the step 206. For instance, if the body temperature fluctuation value exceeds a certain threshold, the wearable bracelet can determine that the current phase of the physiological cycle of the user has varied, and hence determine the actual physiological cycle data of the user in combination with the predicted physiological cycle data.

In addition, the user may also input the basic physiological cycle data into the wearable bracelet manually, so that the wearable bracelet can obtain basic physiological cycle data with higher accuracy for detecting actual physiological cycle data of the user in a next time. Thus, the wearable bracelet can correct error in the physiological index detection, and hence improve the accuracy of the physiological index detection.

Of course, an analysis model on the physiological indexes of the user may also be established in the wearable bracelet to analyze the physiological indexes of the user inputted by the user or detected by the wearable bracelet, e.g., body temperature analysis and menstruation analysis, so that the user can understand his or her health condition more comprehensively and conveniently.

The method for detecting the physiological indexes, provided by the second embodiment of the present disclosure, includes: obtaining the body temperature fluctuation value of the user, where the body temperature fluctuation value includes the difference value of the first difference value between the current shell temperature of the user and the basal body temperature of the user and the second difference value between the current ambient temperature and the ambient reference temperature; and subsequently, correcting the predicated physiological cycle data according to the body temperature fluctuation value of the user to determine and output the actual physiological cycle data of the user, and hence to determine the current physiological indexes of the user. The physiological indexes may include the body temperature fluctuation data and/or the physiological cycle data. As the device for detecting the physiological indexes, which employs the method for detecting the physiological indexes provided by the second embodiment of the present disclosure, may determine the physiological indexes of the user in combination with the body temperature fluctuation value of the user, health-related data processing can be more scientifically performed according to the body temperature fluctuation value of the user, so that the user can obtain the physiological indexes quickly and accurately.

Third Embodiment

Figure 4:
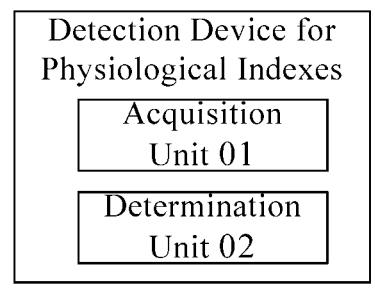
FIG. 4 is a schematic view of a structure of a device for predicting physiological cycles provided by a third embodiment of the present disclosure.

The third embodiment of the present disclosure provides a device for detecting physiological indexes. As illustrated in FIG. 4, the detection device includes: an acquisition unit 01 and a determination unit 02. Description will be given below to the working process of the acquisition unit 01 and the determination unit 02.

The acquisition unit 01 is configured to obtain a body temperature fluctuation value of a user. The body temperature fluctuation value is at least obtained as a first difference value between a current shell temperature of the user and a basal body temperature of the user. Subsequently, the determination unit 02 is configured to determine current physiological indexes of the user according to the body temperature fluctuation value of the user. The physiological indexes, for instance, may include at least one of physiological cycle data and body temperature fluctuation data.

When the physiological indexes include the body temperature fluctuation data, the determination unit 02 determines that the body temperature fluctuation data of the user is normal if the body temperature fluctuation value is within a pre-configured normal temperature range. The determination unit 02 determines that the body temperature fluctuation data of the user is comparatively high if the body temperature fluctuation value is within a pre-configured high temperature range (e.g., a positive temperature range). The determination unit 02 determines that the body temperature fluctuation data of the user is comparatively low if the body temperature fluctuation value is within a pre-configured low temperature range (e.g., a negative temperature range).

Figure 5:
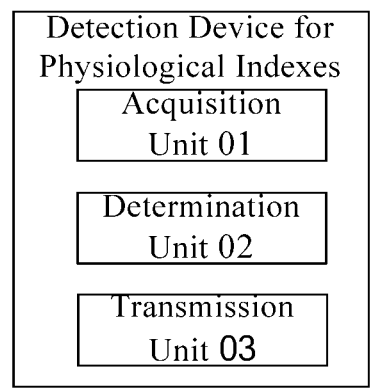
FIG. 5 is a schematic view of another structure of the device for predicting physiological cycles provided by the third embodiment of the present disclosure.

In addition, as illustrated in FIG. 5, the detection device may further include a transmission unit 03. After the determination unit 02 determines the body temperature fluctuation data, the transmission unit 03 feeds back the body temperature fluctuation data to the user through at least one of a display, an indicator light and specified music, or sends the body temperature fluctuation data to client devices of other users via wireless or wired connection.

Moreover, the environment surrounding the user may be varied in real time and the body temperature of the user may also be affected by the ambient temperature. Thus, in order to more accurately detect the current physiological indexes of the user, the variation factor of the ambient temperature may be considered in the process of calculating the body temperature fluctuation value of the user. In order to achieve this goal, the body temperature fluctuation value may be obtained by the first difference value between the current shell temperature of the user and the basal body temperature of the user and the second difference value between the current ambient temperature and the ambient reference temperature. In this case, the determination unit 02 may determine the current physiological indexes of the user according to the difference value between the first difference value and the second difference value.

Figure 6:
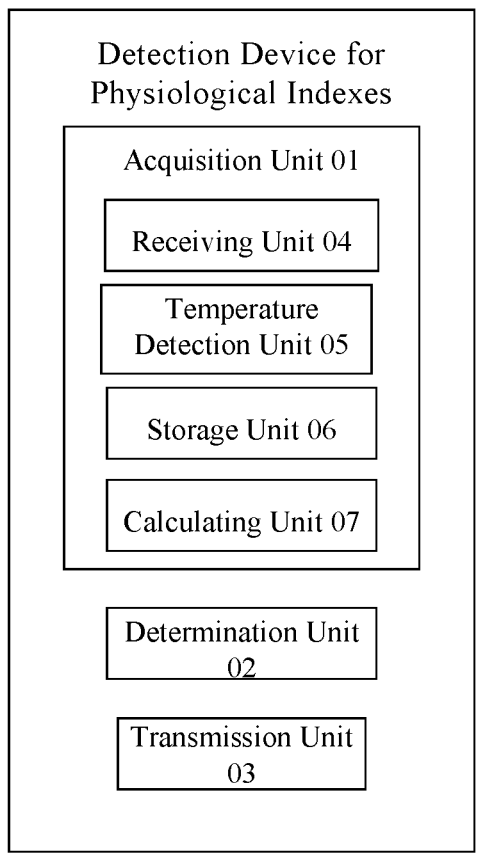
FIG. 6 is a schematic view of yet another structure of the device for predicting physiological cycles provided by the third embodiment of the present disclosure.

Furthermore, as illustrated in FIG. 6, the acquisition unit 01 of the device may further include a receiving unit 04, a temperature detection unit 05, a storage unit 06 and a calculating unit 07. The working process of the device as shown in FIG. 6 may be as follows.

When the physiological indexes include the physiological cycle data, the receiving unit 04 may receive the basic physiological cycle data of the user (for instance, receiving the basic physiological cycle data inputted by the user). The basic physiological cycle data includes the number of days of one menstrual cycle, the starting date of menstruation and the end date of menstruation. The temperature detection unit 05 detects the shell temperature of the user within a first predetermined time window before this physiological index detection and a current shell temperature of the user, and sends the obtained data to the storage unit 06. The calculating unit 07 calculates an average value of the shell temperature of the user within the first predetermined time window based on the detected shell temperature of the user within the first predetermined time window stored in the storage unit 06, and determines the average value of the shell temperature of the user to be a basal body temperature of the user. The temperature detection unit 05 detects an ambient temperature within a second predetermined time window before this physiological index detection and a current ambient temperature, and sends the obtained data to the storage unit 06. The calculating unit 07 determines the first difference value between the current shell temperature of the user stored in the storage unit 06 and the basal body temperature of the user, where the first different value is the body temperature fluctuation value.

Alternatively, the calculating unit 08 may also calculate an average value of the ambient temperature within the second predetermined time window according to the detected ambient temperature within the second predetermined time window stored in the storage unit 06, and determine the average value of the ambient temperature within the second predetermined time window to be the ambient reference temperature. The calculating unit 07 determines a second difference value between the current ambient temperature and the ambient reference temperature, and takes a difference value between the first difference value and the second difference value as the body temperature fluctuation value.

The determination unit 02 may predict a current physiological cycle of the user according to the basic physiological cycle data of the user to obtain predicated physiological cycle data, and correct the predicated physiological cycle data according to the body temperature fluctuation value of the user to determine actual physiological cycle data of the user.

The detection device for detecting the physiological indexes, provided by the embodiment of the present disclosure, may acquire the body temperature fluctuation value of the user, where the body temperature fluctuation value includes the first difference value between the current shell temperature of the user and the basal body temperature of the user, or the body temperature fluctuation value includes the difference value of the first difference value between the current shell temperature of the user and the basal body temperature of the user and the second difference value between the current ambient temperature and the ambient reference temperature. Thus, the detection device further determines the current physiological indexes of the user according to the body temperature fluctuation value of the user, where the physiological indexes may include the body temperature fluctuation data and/or the physiological cycle data. As the detection device for detecting the physiological indexes can determine the physiological indexes of the user in combination with the body temperature fluctuation value of the user, health-related data processing can be more scientifically performed according to the body temperature fluctuation value of the user, so that the user can obtain the physiological indexes quickly and accurately.

Fourth Embodiment

Figure 7:
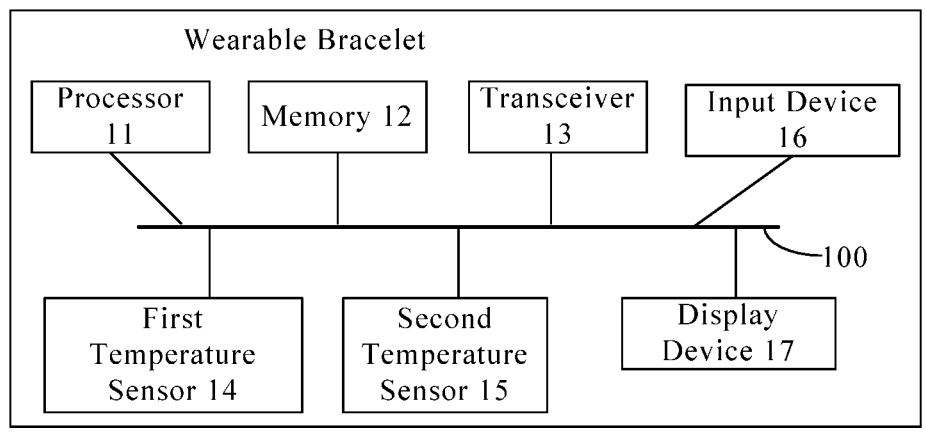
FIG. 7 is a schematic view of a structure of a wearable bracelet provided by a fourth embodiment of the present disclosure.

The fourth embodiment of the present disclosure provides an electronic device including elements for achieving various functional units in the detection device for detecting the physiological indexes provided by the third embodiment. In the embodiment, the electronic device, for instance, may be a wearable bracelet. As illustrated in FIG. 7, the wearable bracelet includes a processor 11, a memory 12, a transceiver 13, a first temperature sensor 14, a second temperature sensor 15, an input device 16, a display device 17 and a bus 100.

The determination unit 02 and the calculating unit 07 in the third embodiment may be achieved by the processor 11 in the embodiment. The storage unit 06 in the third embodiment may be achieved by the memory 12 in the embodiment. The transmission unit 03 may be achieved by the transceiver 13 in the embodiment. The temperature detection unit 05 in the third embodiment may be achieved by the first temperature sensor 14 and the second temperature sensor 15 in the embodiment. For instance, the first temperature sensor 13 may be disposed at a position on an inner side of the wearable bracelet to make contact with the skin of the user, e.g., the wrist skin or the underarm skin, and is configured to sense the shell temperature. The second temperature sensor 14 may be disposed at a position on an outer side of the wearable bracelet to have contact with the external environment, and is configured to sense the ambient temperature.

The receiving unit 04 in the third embodiment may be achieved by the input device 16. The input device 16 may be configured to receive an inputted number or character information (e.g., the basic physiological cycle data inputted by the user), and produce button signal input relevant to user settings and function control of the wearable bracelet. Specifically, the input device 16 may include a touch panel and other input devices.

The display device 17 may be configured to display information inputted by the user or information provided for the user and various menus of the wearable bracelet. The display device 17 may include a display panel which is, for instance, arranged in the form of liquid crystal display (LCD) or organic light-emitting diode (OLED), etc.

For instance, the display device 17 of the wearable bracelet may be a small LCD and may also be an LED light array. The input device 16 of the wearable bracelet may include at least one button which is configured for information display and function selection. Specifically, information such as date, time, body temperature and physiological cycle data may be selected through a short press on the button. The wearable bracelet can be switched to a data recording mode through a long press on the button. In this case, physiological cycle data options such as the starting of menstruation, the end of menstruation and ovulation may be switched to and displayed through the short press on the button. When a corresponding physiological cycle data option is switched to, the current date and the current state under the physiological cycle data option may be recorded through the long press on the button. The wearable bracelet exits from a recording interface automatically if the long press on the button is not performed for a period of time, and no recording is performed.

In addition, the processor 11, the memory 12, the transceiver 13, the first temperature sensor 14, the second temperature sensor 15, the input device 16 and the display device 17 may be connected and communicated with each other through the bus 100.

The foregoing is only the illustrative embodiments of the present disclosure and not intended to limit the scope of protection of the present disclosure. The scope of protection of the present disclosure should be defined by the appended claims.

The present disclosure claims the benefits of Chinese patent application No. 201510359441.5, which was filed on Jun. 25, 2015 and is incorporated herein in its entirety by reference as part of this application.

What is claimed is:

1. A method for detecting physiological indexes for providing suggestion of adding or taking off clothes for a user, comprising:
   detecting, via a first temperature sensor, a current shell temperature associated with the user,
   detecting, via a second temperature sensor, an ambient temperature within a second predetermined time window before current physiological index determination and the current ambient temperature;
   calculating, via a processor, an average value of the ambient temperature within the second predetermined time window, and determining the average value of the ambient temperature within the second predetermined time window to be the ambient reference temperature;
   obtaining, via the processor, the body temperature fluctuation value by a first difference value between the current shell temperature associated with the user and a basal body temperature associated with the user and a second difference value between the current ambient temperature and the ambient reference temperature;

determining, via the processor, a current physiological index associated with the user based on a difference value between the first difference value and the second difference value; and displaying, via a display device, suggestion of adding clothes for the user when the processor determines that −1° C.<the body temperature fluctuation value <−0.5° C.; or displaying, via the display device, suggestion of taking off-a clothes for the user when the processor determines that 0.5° C.<the body temperature fluctuation value <1° C.

2. The method according to claim 1, wherein:
the physiological index includes physiological cycle data;
prior to determining the current physiological index associated with the user, the method further comprises obtaining, via an input device, basic physiological cycle data associated with the user, wherein the basic physiological cycle data includes a quantity of days of one menstrual cycle, a starting date of menstruation and an end date of menstruation; and determining, via the processor, the current physiological index associated with the user based on the body temperature fluctuation value associated with the user includes:
  predicting, via the processor, a current physiological cycle associated with the user based on the basic physiological cycle data associated with the user to obtain predicted physiological cycle data; and
  correcting, via the processor, the predicted physiological cycle data based on the body temperature fluctuation value associated with the user to determine actual physiological cycle data associated with the user.

3. The method according to claim 2, wherein obtaining the basic physiological cycle data associated with the user includes:
receiving, via the input device, the basic physiological cycle data inputted by the user.

4. The method according to claim 1, wherein:
the physiological index includes body temperature fluctuation data; and
determining, via the processor, the current physiological index associated with the user based on the body temperature fluctuation value associated with the user includes:
  determining, via the processor, that the body temperature fluctuation data associated with the user is normal if the body temperature fluctuation value is within a pre-configured normal temperature range;
  determining, via the processor, that the body temperature fluctuation data associated with the user is comparatively high if the body temperature fluctuation value is within a pre-configured positive temperature range; and
  determining, via the processor, that the body temperature fluctuation data associated with the user is comparatively low if the body temperature fluctuation value is within a pre-configured negative temperature range.

5. The method according to claim 4, wherein after determining the current physiological index associated with the user based on the body temperature fluctuation value associated with the user, the method further comprises:
sending back, via a transceiver, the body temperature fluctuation data to the user through at least one of a display, an indicator light and specified music; or
sending, via the transceiver, the body temperature fluctuation data to client devices of other users via wireless or wired connection.

6. The method according to claim 1, further comprising obtaining the first difference value, wherein obtaining the first difference value includes:
detecting, via the first temperature sensor, the shell temperature associated with the user within a first predetermined time window before the current physiological index determination and the current shell temperature associated with the user;
calculating, via the processor, an average value of the shell temperature associated with the user within the first predetermined time window, and determining the average value of the shell temperature associated with the user to be the basal body temperature associated with the user; and
determining, via the processor, a difference value between the current shell temperature associated with the user and the basal body temperature associated with the user to be the first difference value.

7. A device for detecting physiological indexes for providing suggestion of adding or taking off clothes for a user, comprising:
a first temperature sensor configured to detect a shell temperature associated with the user;
a second temperature sensor configured to detect an ambient temperature within a second predetermined time window before the current physiological index determination and the current ambient temperature;
a processor configured to
  calculate an average value of the ambient temperature within the second predetermined time window, and determine the average value of the ambient temperature within the second predetermined time window to be the ambient reference temperature,
  obtain a body temperature fluctuation value associated with a user, wherein the body temperature fluctuation value is obtained by a first difference value between a current shell temperature associated with the user and a basal body temperature associated with the user detected by the first temperature sensor and a second difference value between the current ambient temperature and the ambient reference temperature detected by the second temperature sensor; and
  determine a current physiological index based on a difference value between the first difference value and the second difference value,
a display device configured to
  display suggestion of adding s-clothes for the user when the processor determines that −1° C.<the body temperature fluctuation value <−0.5° C.; and
  display suggestion of taking off a-clothes for the user when the processor determines that 0.5° C.<the body temperature fluctuation value <1° C.

8. The device according to claim 7, wherein:
the physiological index includes physiological cycle data;
an input device is configured to obtain basic physiological cycle data associated with the user, wherein the basic physiological cycle data includes a quantity of days of one menstrual cycle, a starting date of menstruation and an end date of menstruation; and
the processor is configured to:
  predict a current physiological cycle associated with the user based on the basic physiological cycle data associated with the user to obtain predicted physiological cycle data; and correct the predicted physiological cycle data based on the body temperature fluctuation value associated with the user to determine actual physiological cycle data associated with the user.

9. The device according to claim 8, wherein:
the input device is configured to receive the basic physiological cycle data inputted by the user.

10. The device according to claim 7, wherein:
the physiological index includes body temperature fluctuation data; and
the processor determines that the body temperature fluctuation data associated with the user is normal if the body temperature fluctuation value is within a pre-configured normal temperature range;
the processor determines that the body temperature fluctuation data associated with the user is comparatively high if the body temperature fluctuation value is within a pre-configured positive temperature range; and
the processor determines that the body temperature fluctuation data associated with the user is comparatively low if the body temperature fluctuation value is within a pre-configured negative temperature range.

11. The device according to claim 10, wherein:
the device further comprises a transceiver;
the transceiver is configured to send back the body temperature fluctuation data to the user through at least one of a display, an indicator light and specified music; or
the transceiver is configured to send the body temperature fluctuation data to client devices of other users via wireless or wired connection.

12. The device according to claim 7, wherein:
the device further includes a memory;
the first temperature sensor is configured to detect the shell temperature associated with the user within a first predetermined time window before the current physiological index determination and the current shell temperature associated with the user, and send the detected data to the memory; and
the processor is configured to:
calculate an average value of the shell temperature associated with the user within the first predetermined time window based on the detected shell temperature associated with the user within the first predetermined time window stored in the memory;
determine the average value of the shell temperature associated with the user to be the basal body temperature associated with the user; and
determine a difference value between the current shell temperature associated with the user stored in the memory and the basal body temperature associated with the user to be the first difference value.

13. The device according to claim 7, wherein the device for detecting the physiological indexes is a wearable bracelet.

14. The method according to claim 2, further comprising obtaining the first difference value, wherein obtaining the first difference value includes:
detecting, via the first temperature sensor, the shell temperature associated with the user within a first predetermined time window before the current physiological index determination and the current shell temperature associated with the user;
calculating, via the processor, an average value of the shell temperature associated with the user within the first predetermined time window, and determining, via the processor, the average value of the shell temperature associated with the user to be the basal body temperature associated with the user; and
determining, via the processor, a difference value between the current shell temperature associated with the user and the basal body temperature associated with the user to be the first difference value.

15. The method according to claim 2, wherein:
the body temperature fluctuation value is obtained by the first difference value between the current shell temperature associated with the user and the basal body temperature associated with the user and a second difference value between a current ambient temperature and an ambient reference temperature; and
determining, via the processor, the current physiological index associated with the user based on the body temperature fluctuation value associated with the user includes:
determining, via the processor, the current physiological index associated with the user based on a difference value between the first difference value and the second difference value.

16. The device according to claim 8, wherein:
the body temperature fluctuation value is obtained by the first difference value between the current shell temperature associated with the user and the basal body temperature associated with the user and a second difference value between a current ambient temperature and an ambient reference temperature; and
the processor is configured to determine the current physiological index associated with the user based on a difference value between the first difference value and the second difference value.

* * * * *